United States Patent
Ibrahim

(10) Patent No.: US 10,070,939 B2
(45) Date of Patent: Sep. 11, 2018

(54) METHODS FOR PERFORMING MINIMALLY INVASIVE TRANSFORAMINAL LUMBAR INTERBODY FUSION USING GUIDANCE

(71) Applicant: Zaki G. Ibrahim, Greenwood Village, CO (US)

(72) Inventor: Zaki G. Ibrahim, Greenwood Village, CO (US)

( * ) Notice: Subject to any disclaimer, the term of this patent is extended or adjusted under 35 U.S.C. 154(b) by 0 days.

(21) Appl. No.: 15/366,421

(22) Filed: Dec. 1, 2016

(65) Prior Publication Data

US 2017/0156816 A1    Jun. 8, 2017

Related U.S. Application Data

(60) Provisional application No. 62/263,547, filed on Dec. 4, 2015.

(51) Int. Cl.
| | | |
|---|---|---|
| A61B 17/88 | (2006.01) | |
| A61B 90/00 | (2016.01) | |
| A61B 17/02 | (2006.01) | |
| A61B 34/30 | (2016.01) | |
| A61B 17/86 | (2006.01) | |
| A61B 17/56 | (2006.01) | |

(52) U.S. Cl.
CPC ............ *A61B 90/39* (2016.02); *A61B 17/025* (2013.01); *A61B 17/864* (2013.01); *A61B 34/30* (2016.02); *A61B 2017/0256* (2013.01); *A61B 2017/564* (2013.01); *A61B 2090/3916* (2016.02); *A61B 2090/3991* (2016.02)

(58) Field of Classification Search
CPC ... A61B 90/39; A61B 3430/30; A61B 17/025; A61B 17/864; A61B 2090/3916; A61B 2090/3991; A61B 2017/0256; A61B 2017/564
USPC .............. 606/265, 279, 304, 90, 96, 97, 105
See application file for complete search history.

(56) References Cited

U.S. PATENT DOCUMENTS

| | | | | |
|---|---|---|---|---|
| 2006/0030850 A1* | 2/2006 | Keegan | ............... | A61B 17/0293 606/60 |
| 2007/0016219 A1* | 1/2007 | Levine | ................... | A61B 90/39 606/99 |
| 2009/0187194 A1* | 7/2009 | Hamada | ............. | A61B 17/7001 606/104 |
| 2009/0287222 A1* | 11/2009 | Lee | .................... | A61B 17/1615 606/130 |
| 2010/0331883 A1* | 12/2010 | Schmitz | ............. | A61B 10/0275 606/249 |
| 2011/0301647 A1* | 12/2011 | Hua | ................... | A61B 17/7083 606/279 |
| 2014/0025088 A1* | 1/2014 | Zarrouk | ............. | A61B 19/2203 606/130 |

\* cited by examiner

*Primary Examiner* — Pedro Philogene
*Assistant Examiner* — David C Comstock
(74) *Attorney, Agent, or Firm* — Lathrop Gage LLP

(57) ABSTRACT

A minimally invasive transforaminal lumbar interbody fusion surgery method includes sequential steps of (a), aided by a guidance system, placing a guide wire in each pedicle of each vertebra of each spinal segment to be fused in a transforaminal lumbar interbody fusion surgery, (b) replacing one or more of the guide wires with respective pedicle markers, and (c) performing the minimally invasive transforaminal lumbar interbody fusion surgery using the pedicle markers and remaining ones of the guide wires.

20 Claims, 5 Drawing Sheets

METHODS FOR PERFORMING MINIMALLY INVASIVE TRANSFORAMINAL LUMBAR INTERBODY FUSION USING GUIDANCE

CROSS-REFERENCE TO RELATED APPLICATIONS

The present application claims the benefit of priority from U.S. Provisional Application No. 62/263,547 filed Dec. 4, 2015, which is incorporated herein by reference in its entirety.

BACKGROUND

Traditional "open" surgical approaches to the spine and other organs typically involve extended longitudinal incisions, significant tissue disruption, and substantial blood loss. Recovery from these types of procedures may be prolonged and may involve significant morbidity. In addition to the above intraoperative difficulties and problems with rehabilitation, there is increasing evidence that "open" approaches may significantly devitalize tissue, predisposing to higher rates of infection.

In response to these problems and as a direct result of rising healthcare costs, increasing pressure to reduce hospital stays and improve patient recovery, physicians have expressed significant interest in performing surgical procedures through less invasive techniques. Minimally invasive surgery (MIS) is a term which encompasses a wide range of surgical interventions. All of these surgical interventions involve accomplishing a surgical goal which is similar to that of a traditional "open" technique using a technique which involves much less disruptive surgical dissection.

In no medical subspecialty has this type of approach sparked more interest than in that of spinal surgery. MIS approaches have been at the forefront of much recent literature. MIS has appeared to substantially decrease blood loss, complications, recovery times and hospital stays in comparison to traditional methods for procedures such as discectomy, decompression, and cervical and lumbar fusions.

SUMMARY

In an embodiment, a minimally invasive transforaminal lumbar interbody fusion surgery method includes a step of placing a guide wire in each pedicle of each vertebra of each spinal segment to be fused in a transforaminal lumbar interbody fusion surgery. This step is aided by a guidance system. Next, one or more of the guide wires is replaced with respective pedicle markers. Next, the minimally invasive transforaminal lumbar interbody fusion surgery is performed using the pedicle markers and remaining ones of the guide wires.

DETAILED DESCRIPTION OF THE EMBODIMENTS

Figure 1:
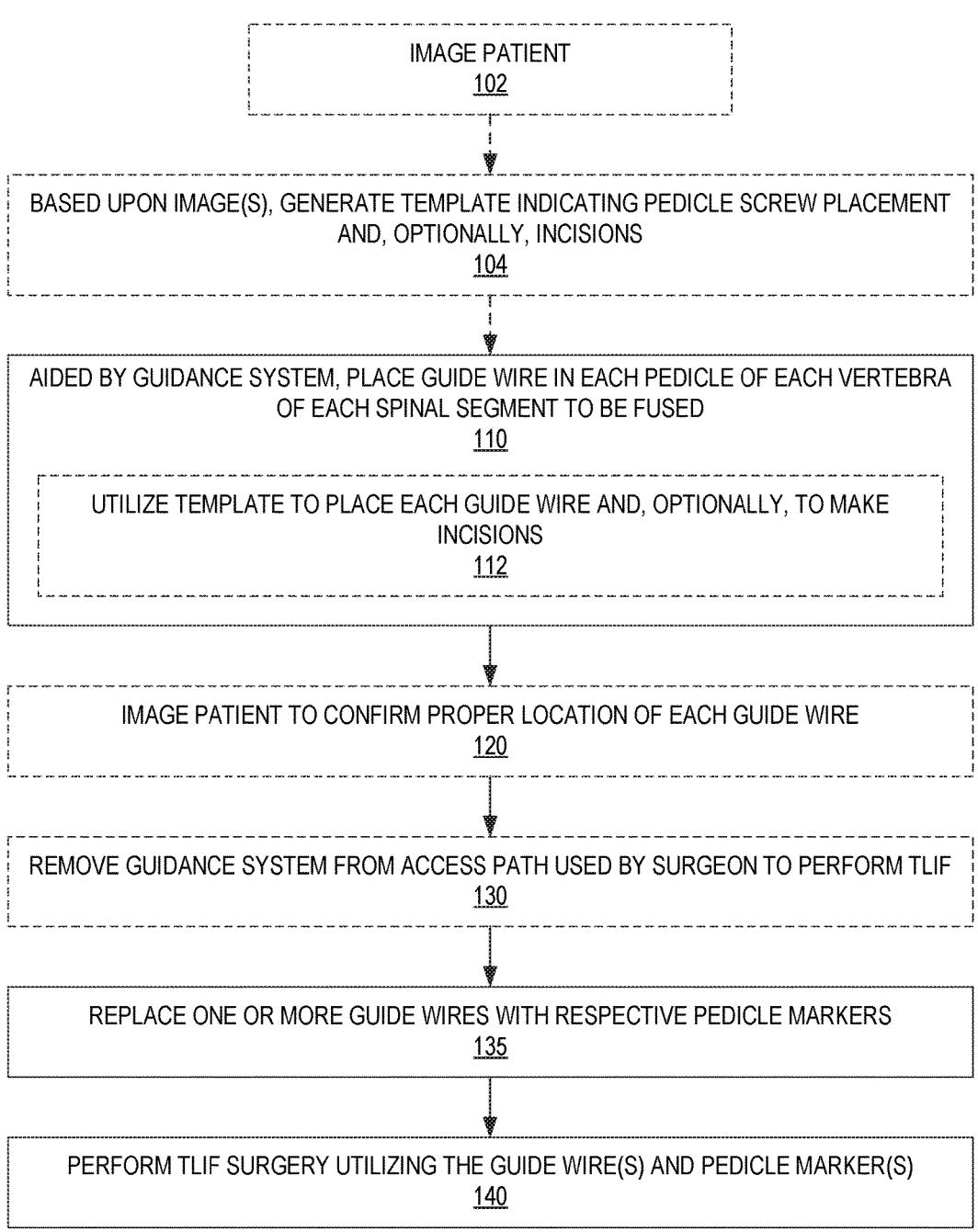
FIG. 1 illustrates a minimally invasive transforaminal lumbar interbody fusion (TLIF) surgery method that uses guidance, according to an embodiment.

While there has been an explosion of interest in minimally invasive spinal surgery, significant shortcomings remain. Because limited exposures obstruct direct visualization of anatomic structures, minimally invasive (MIS) procedures have historically been highly x-ray dependent. In a classic case of conventional minimally invasive spinal surgery, two C-arm fluoroscopes (intraoperative x-ray machines capable of providing real-time images to the surgeon) are utilized by the operative team to simultaneously provide real-time images in the AP and lateral planes. In conventional minimally invasive spinal surgery, these simultaneous images in perpendicular planes are necessary in order to guide accurate implantation of instrumentation into anatomic structures.

However, the use of fluoroscopy in perpendicular planes is far from an elegant method of providing visualization to the surgeon. First, these machines are large and cumbersome. The surgeon often finds himself struggling to place hardware while avoiding contact with a fluoroscope or attempting to avoid the x-ray beam. Oftentimes, this may result in the surgeon contorting himself awkwardly in an effort to accurately place instrumentation. Second, the ability of fluoroscopy to accurately identify underlying anatomic structures may be significantly limited by patient characteristics such as osteoporosis, anatomic variability, or obesity. The presence of any of these patient-specific variations may substantially limit the ability of the surgeon to accurately place instrumentation. Finally, the use of dual C-arms in perpendicular planes may expose the patient to excessive radiation during the procedure. Further, over the course of many such surgical interventions, the operative team may be exposed to an extremely high cumulative dose of radiation.

As a potential solution to the concerns raised above, surgeons have turned to various guidance systems in order to improve accuracy and decrease radiation exposure to the patient and the operative team. While these guidance systems typically offer increased accuracy and decreased radiation, a shortcoming of many of these systems is that all instrumentation must be placed at one time, once the guidance technology has successfully been matched to the patient's anatomy and before the surgical intervention has altered the underlying anatomy significantly.

Placing instrumentation at the beginning of a surgical intervention may significantly alter a surgeon's technique. Further, placement of any instrumentation at the beginning of a case, prior to any alteration of the underlying anatomy, may introduce a significant intraoperative obstruction. This may prevent the surgeon from adequately decompressing neural structures or from performing a necessary intradiscal fusion, especially with current minimally invasive fixation systems which typically utilize a tower coupled to the underlying screw. Alternatively, placement of instrumentation at the end of a case, after the decompression/intradiscal work has been done, may result in inaccurate matching of the guidance technology to the underlying anatomy. Also, advantages provided by placement of instrumentation (ability to compress and distract as necessary) are not available with this method.

FIG. 1 illustrates one exemplary minimally invasive transforaminal lumbar interbody fusion (TLIF) surgery method 100 that uses guidance. Method 100 may be used to perform minimally invasive TLIF of one spinal segment or of two or more adjacent spinal segments. Method 100 utilizes guidance technology that allows the surgeon significantly more access and visualization of the surgical bed than methods previously described. Method 100 benefits from guidance to precisely place guide wires, and pedicle markers over certain guidewires, during the initial stages of the operative intervention, without encumbering the surgeon during the remainder of the operative intervention. In comparison with non-guidance minimally invasive surgery methods, method 100 significantly enhances precision of instrumentation placement and markedly limits radiation exposure.

Method 100 allows for precise partial placement of instrumentation on a non-working side of the spine while maintaining unencumbered visualization for the surgeon on the working side of the spine, such that adequate decompression and fusion may be accomplished without obstructing hardware. Since method 100 at least mostly limits the use of guidance to the initial stages of the operative intervention, method 100 significantly diminishes x-ray exposure to the patient and the operative team.

Herein, the "working side" of the spine refers to the side of the spine from which the surgeon inserts tools to access the intervertebral disc space of a spinal segment to be fused, and the "non-working side" is the side opposite to the working side. In a typical example, the working side is the more symptomatic side or the side with more significant compression of neural elements.

In certain embodiments, method 100 further allows for distraction of the intervertebral disc space by applying distracting tools into the intervertebral disc space from the working side while simultaneously applying distraction across instrumentation on the non-working side. This distraction is valuable in allowing for further indirect decompression of the neural elements and restoration of anatomic alignment.

In one embodiment, method 100 allows the surgeon to utilize pedicle markers for precise knowledge of the anatomy. These pedicle markers are typically low profile screws (similar to facet screws) which may be threaded into the pedicle over a localizing guidewire. They allow the surgeon to maintain knowledge of the precise location of the pedicle on the "working side" throughout the case. This assists the surgeon in making precise bony cuts through the adjacent facet joint and in locating the pedicle in order to place a pedicle screw.

In a step 110, method 100 utilizes a guidance system to place guide wires in each pedicle of each vertebra of each spinal segment to be fused. In an optional step 130, the guidance system is removed from the patient. In a step 135, the surgeon replaces one or more of the guide wires with respective pedicle markers. The pedicle markers are low profile and less obtrusive to the work performed by the surgeon. In a step 140, the surgeon utilizes the pedicle marker(s) and remaining guide wire(s) to perform the TLIF surgery. The surgeon may enjoy improved access to the surgery location due to the less obtrusive pedicle markers inserted in step 135. Step 140 may utilize surgical techniques known in the art.

Herein, a "surgeon" may refer to one or more humans, a robotic system, or a combination thereof.

In one embodiment, step 110 includes a step 112 of utilizing a template to place each guide wire, and optionally to make incisions needed to perform the TLIF surgery. This template is based upon imaging of the patient performed prior to step 110, such as a pre-operative computed tomography (CT) scan of the patient. The template may indicate the intended trajectory of a pedicle screw into each pedicle and step 110 may place each guide wire according to such a trajectory. The template may also indicate the position and sizes of incisions.

Optionally, method 100 includes a step 102 of imaging the patient and a step 104 of generating the template of step 112 based upon one or more images captured in step 102.

In an embodiment, method 100 includes a step 120 after step 110 and before step 130. Step 120 images the patient to confirm proper location of the guide wires placed in the patient in step 110.

Method 100 utilizes guidance to precisely place the guide wires in step 110 such that TLIF surgery performed in step 140 may utilize this precise guide wire placement without relying on further guidance, or at least with only minimal use of further guidance.

In one exemplary use scenario, method 100 is performed using the Jackson frame (a specialized radiolucent table designed specifically for spinal surgery). Frequently, TLIF procedures are performed at the lumbosacral junction. If method 100 includes fusion at the lumbosacral junction, the table may be modified preoperatively to allow some degree of reverse Trendelenburg positioning. This may be done by placing the positioning pins at the head of the table in a high slot and placing the positioning pins at the foot of the table in a low slot. In this way some degree of reverse Trendelenburg position is immediately gained which in may be increased during the procedure so that the surgical team is not working at an excessive "angle" in trying to work on the lumbosacral junction. In this exemplary use scenario, the patient is strapped tightly to the table over the chest and thighs to allow the table to be tilted in order to allow the surgeon access through a minimally-invasive technique.

Figure 2:
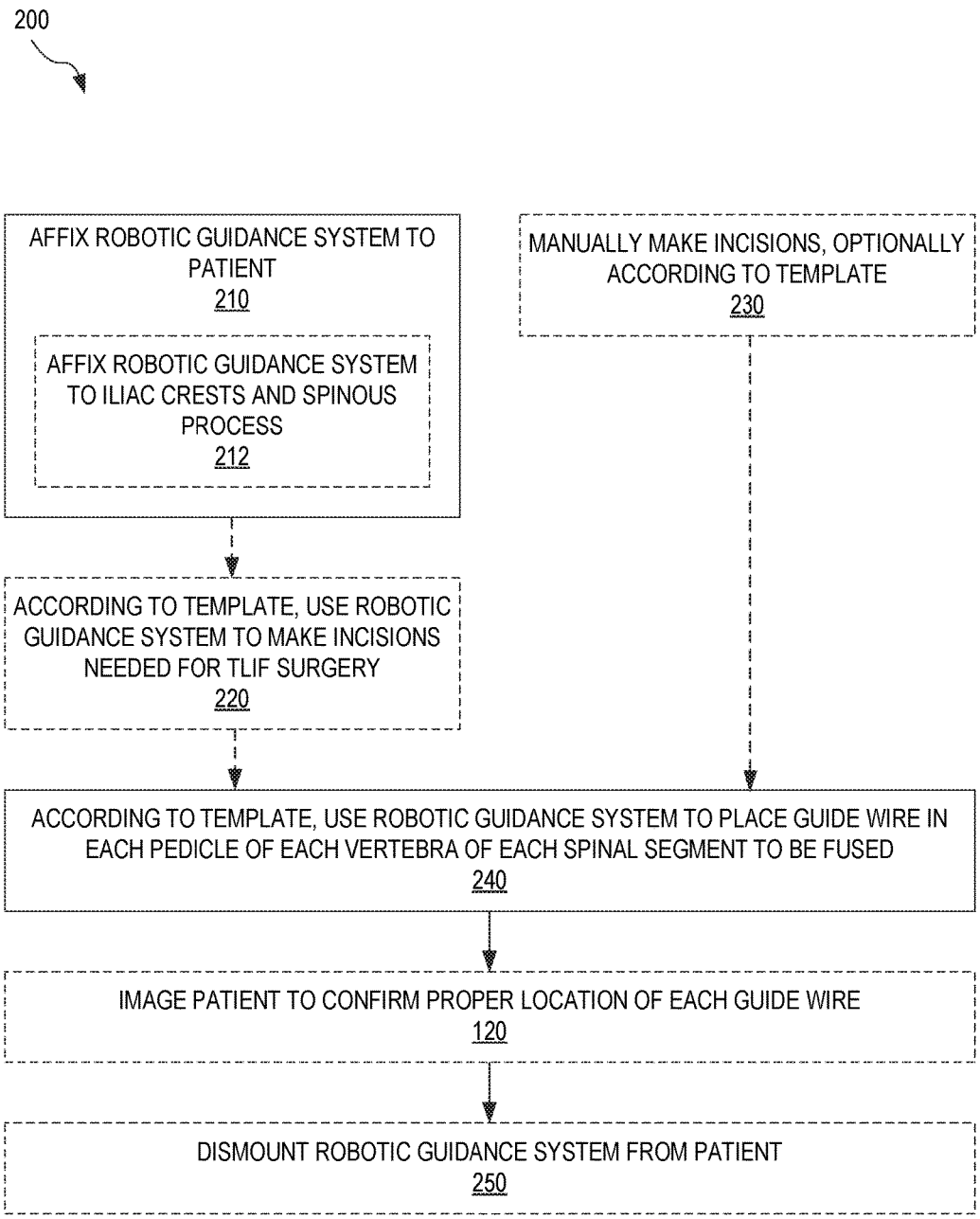
FIG. 2 illustrates a robotic guidance method that is an embodiment of a portion of the method of FIG. 1, according to an embodiment.

FIG. 2 illustrates one exemplary robotic guidance method 200 that is an embodiment of steps 110 and 130, and optionally step 120, of method 100. Method 200 includes a step 210 of affixing a robotic guidance system to the patient. Step 210 may implement a step 212 of affixing the robotic guidance system to the iliac crest on both sides of the spine and to a spinous process of the spine, for example a spinous process that is superior to the spinal segments to be fused.

Method 100 includes either a step 220 or a step 230. In step 220, the robotic guidance system makes the incisions needed for the TLIF surgery according to a template, such as the template discussed above in reference to FIG. 1. In one example of step 220, the template extrapolates the trajectory of pedicle screws through the skin to define the locations of incisions. In step 230, the surgeon manually makes the incisions needed for the TLIF surgery, optionally according to such a template.

In a step 240, the robotic guidance system utilizes the template to place a guide wire in each pedicle of each vertebra of each spinal segment to be fused. Step 240 is an embodiment of step 110 implementing step 112.

Method 200 may perform step 120 after step 240 to confirm proper location of the guide wires placed in step 240.

In an optional step 250, the robotic guidance system is dismounted from the patient. Step 250 is an embodiment of step 130.

In one example, method 200 utilizes the Mazor Rennaisance® guidance system by Mazor Robotics. The Mazor Rennaisance® guidance system allows the surgeon to preoperatively template the intended orientation of implanted hardware on a virtual blueprint based upon a CT scan of the patient's anatomy. The Mazor software allows the surgeon to extrapolate the trajectory of the implanted hardware out to where it intersects the skin. This allows the surgeon to precisely plan the location and length of his intended incision. Familiarity with this process allows the surgeon to plan his hardware placement in a manner which minimizes the length of incision and associated tissue destruction while placing hardware accurately in its intended position. For each spinal segment, the incisions used typically, but not always, measure about 3 cm and are placed 3-5 centimeters from the midline on either side of the spine. One of the advantages of the method described herein includes allowing the surgeon the ability to use one (or both) of these incisions to perform lumbar decompression and interbody fusion while maintaining accurate placement of hardware.

Also in this example, the Mazor Guidance system is used intraoperatively at the very beginning of the case to accurately place a guide wire into each pedicle of each vertebra to be included in the fusion. In one implementation, the "Hover-T" frame (by Mazor Robotics) is rigidly attached, in step 210, to the patient through a cephalad spinous process pin and two Shantz screws in the iliac crest. However, any other frame may be utilized so long as it is capable of accurately placing the guide wires. Calibrating x-rays are obtained in the AP and oblique planes with the fiducial 3D marker in place. The Mazor software then matches the preoperative CT scan (such as obtained in step 102) to the patient's anatomy using a registered vertebra. The robot itself is then placed on top of the Hover-T frame, or another frame, and is used to place incisions in step 220 and accurately place, in step 240, a guide wire into each pedicle of each vertebra to be included in the fusion. The robot may be used with the appropriate outrigger to precisely place the incision and the guide wires into the pedicles. Once the guide wires are confirmed ion step 120 to be in precise position (typically by using C-arm in the AP and lateral planes), the Hover-T frame is removed and the Mazor Renaissance Guidance system may be removed from the operating room. Alternatively, the surgeon may elect to keep the Hover-T frame in place and the Mazor Renaissance Guidance system in the room for the duration of the case. This may be helpful in the case of a guidewire becoming dislodged and needing to be replaced.

In another example, method 200 utilizes another guidance system than the Mazor Rennaisance Guidance System.

Figure 3A:
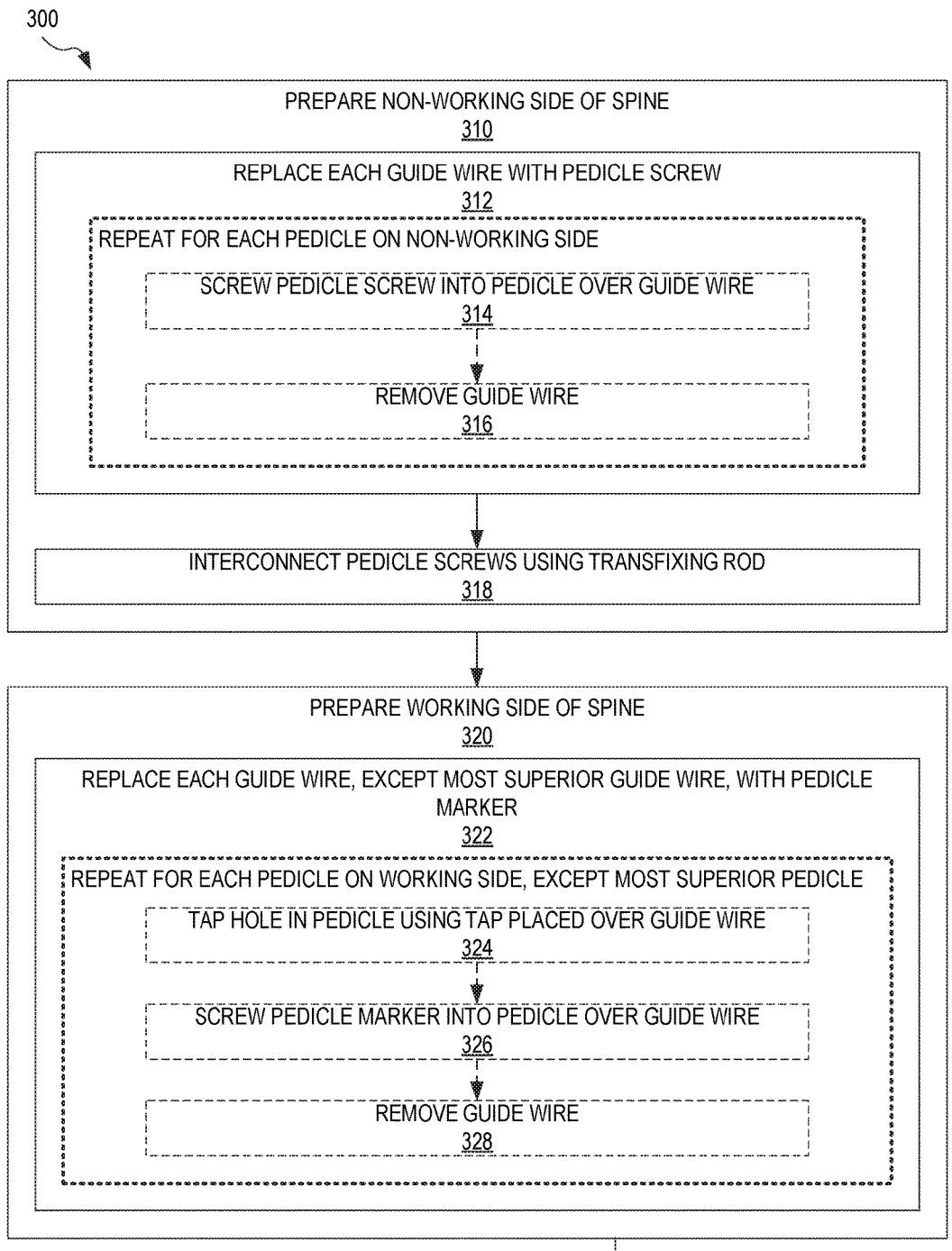
FIGS. 3A and 3B illustrate a method for performing the TLIF surgery of the method of FIG. 1 using guide wires and pedicle markers, according to an embodiment.
Figure 3B:
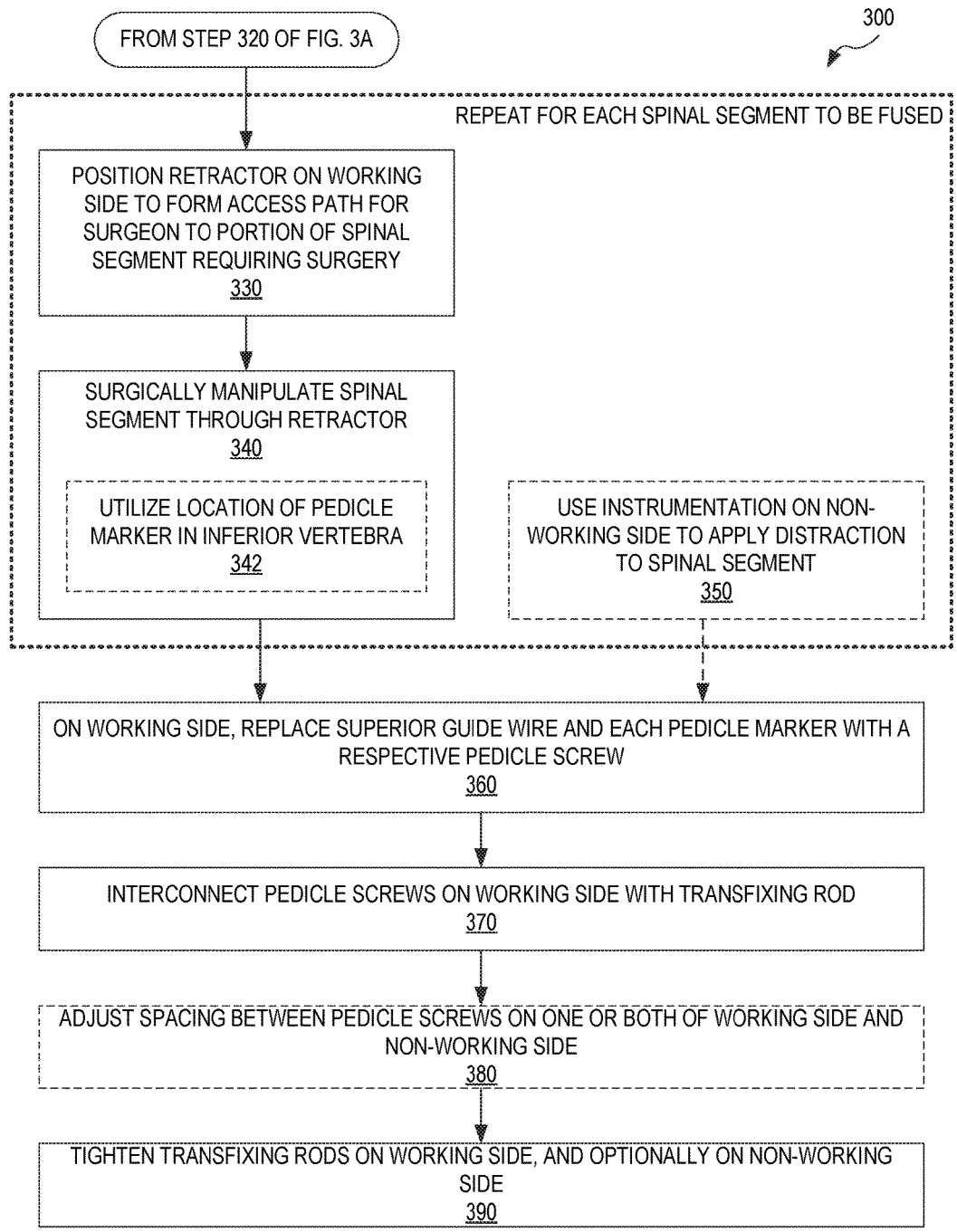

FIGS. 3A and 3B illustrate one exemplary method 300 for performing the TLIF surgery using pedicle markers and a guide wire. Method 300 is an embodiment of step 140 of method 100 and utilizes the pedicle markers placed in step 135 and a single remaining one of the guide wires placed in the patient in step 110. FIGS. 3A and 3B are best viewed together.

In a step 310, method 300 prepares the non-working side of the spine. Step 310 includes a step 312 of replacing each guide wire on the non-working side of the spine with a pedicle screw. In an embodiment, step 312 includes repeating steps 314 and 316 for each guide wire. Step 314 screws a pedicle screw into the pedicle over the guide wire. This typically involves tapping over the guidewire and may involve using tissue protecting tubes to place the screw. Subsequently, step 316 removes the guide wire. Step 310 further includes a step 318 of interconnecting the guide wires using a transfixing rod, such as a transfixing rod known in the art and used to stabilize a spinal segment. The transfixing rod is at least provisionally tightened into place to define the spacing between the pedicles.

In a step 320, method 300 prepares the working side of the spine. Step 320 includes a step 322 of replacing each guide wire on the working side, except for the most superior guide wire, with a pedicle marker. In an embodiment, step 322 includes repeating steps 324, 326, and 328 for each guide wire. Step 324 taps a hole in the pedicle using a tap placed over the guide wire. Step 326 screws the pedicle marker into the pedicle over the guide wire. Subsequently, step 328 removes the guide wire. The superior guidewire does not typically encumber the surgical field and may usually be flexed out of the way. Typically, the bone around the superior guidewire is not tapped until just before placement of the pedicle screw in order to prevent displacement of this guidewire during the case.

Without departing from the scope hereof, the order of steps 310 and 320 may be reversed, or steps 310 and 320 may be performed in an at least partially overlapping fashion.

After performing steps 310 and 320, method 300 repeats steps 330 and 340, and optionally step 350, for each spinal segment to be fused.

In step 330, a retractor is positioned on the working side to form an access path for the surgeon to a portion of the spinal segment requiring surgery. The retractor may be introduced over dilators into the incision on the working side without risk of displacing any of the pedicle markers as they are threaded into the pedicles. If needed, the remaining superior guide wire may be flexed out of the way of the retractor prior to insertion of the retractor.

In step 340, the surgeon surgically manipulates the spinal segment through the retractor. Step 340 may include, for example, removing tissue from the spinal segment and inserting fusion promoting material such as bone graft into the intervertebral disc space. Soft tissue may be gently debrided away from the underlying lamina, pars, and/or facet joint on the working side. The nerve decompression and a minimally-invasive TLIF may then performed using the preferred technique of the surgeon. Step 340 may utilize methods known in the art, such as microscope visualization. Step 340 may implement a step 342 of utilizing the location of the pedicle marker in the inferior vertebra as a reference point. This may be helpful in making the cut in the adjacent facet at the appropriate level.

In optional step 350, the surgeon uses the instrumentation placed on the non-working side in step 310 to apply distraction, or compression, to the spinal segment. Without departing from the scope hereof, step 318 may be performed after step 310, for example immediately prior to step 350, as opposed to being included in step 310. In embodiments of method 300 that do not include step 350, step 318 may be performed at a later stage of method 300, such as in optional step 380 discussed below. It may be beneficial to apply distraction on the non-working side in synchrony with distraction applied to the working side in the disc space. Such combination of distractive forces may significantly mobilize the spine.

A step 360 replaces the superior guide wire on the working side and each pedicle marker on the working side with a respective pedicle screw. The superior guide wire may be replaced by a pedicle screw in the same manner as used for the non-working side in step 312. The pedicle marker may be replaced by a pedicle screw by (a) inserting a guide wire into the pedicle marker, (b) unscrewing the pedicle marker and removing the pedicle marker over the guide wire, and (c) screwing the pedicle screw into the pedicle over the guide wire.

A step 370 interconnects the pedicle screws on the working side with a transfixing rod, as discussed for step 318. The transfixing rod and pedicle screws on the working side cooperate with the transfixing rod and pedicle screws on the non-working side, and further with fusion material placed in the intervertebral disc space(s) in step 340, to stabilize the spinal segment(s).

Optionally, method 300 includes step 380 of adjusting the spacing between pedicle screws on one or both of the working and non-working side, to stabilize the spinal segment in a desired anatomic configuration. For either one of the working and non-working side, step 380 adjusts this spacing by loosening the connection between the transfixing rod and at least one pedicle screw, adjusting the spacing between the pedicle screws, and retightening the connection transfixing rod and the pedicle screws.

In a step 390, the surgeon performs a final tightening of the transfixing rod into the pedicle screws on the working side and, if not yet performed, also on the non-working side.

In one example, method 300 utilizes pedicle screws having a removable guiding section that penetrates the skin of the patient. In this example, method 300 may include removing the removable guiding sections, for example after step 370 or after step 380 (if included).

Figure 4:
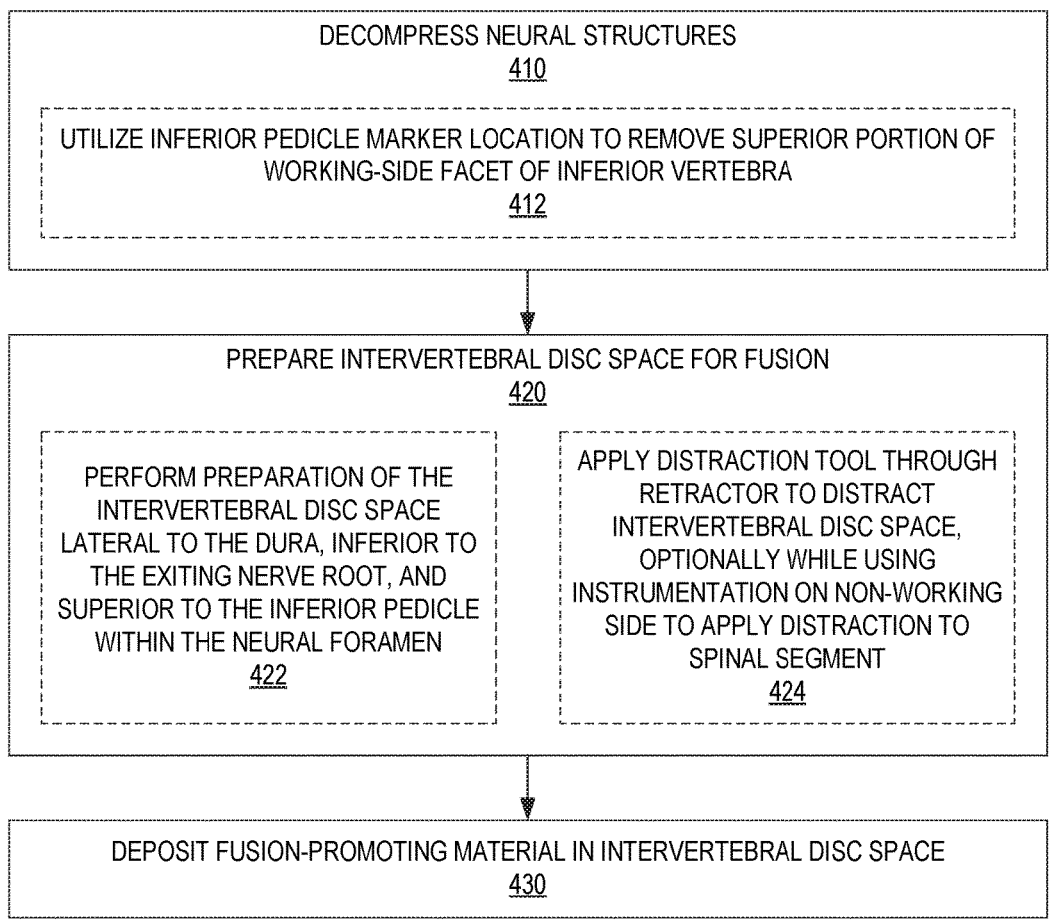
FIG. 4 illustrates a method for surgically manipulating a spinal segment in minimally invasive TLIF surgery, according to an embodiment.

FIG. 4 illustrates one exemplary method 400 for surgically manipulating a spinal segment in minimally invasive TLIF surgery. Method 400 is an embodiment of step 340.

In a step 410, the surgeon decompresses neural structures of the spinal segment. Step 410 may include a step 412 of utilizing the location of the pedicle marker in the inferior vertebra of the spinal segment to remove a superior portion of the working-side facet of the inferior vertebra. Step 410 may utilize microscope visualization.

In one example of step 410, under microscope visualization, a drill or high-speed bur is passed in a curvilinear fashion across the posterior elements of the superior vertebra of the spinal segment. A "trough" is eventually created between the ipsilateral pars and the inferior aspect of the lamina, just adjacent to the spinous process. After multiple passes, only a thin shell of bone remains, and it is easy to osteotomize and remove this fragment of bone by using an osteotome in a twisting fashion. The removed fragment of bone includes the inferior facet on this side. This action brings the superior facet of the inferior vertebra into excellent relief. The superior facet of the inferior vertebra is osteotomized next. For this purpose, the location of the pedicle marker is noted, and a transverse cut is made across this facet, just above the pedicle marker, using the high-speed bur. The superior portion of the facet is easily removed using a twisting motion with an osteotome, leaving only remaining ligamentum flavum and underlying dura and nerve roots. These may then be easily decompressed, under the microscope, according to the needs of the patient. The decompression may be carried across the midline and into the contralateral lateral recess simply by wanding the retractor underneath the spinous process.

In a step 420, the surgeon prepares the intervertebral disc space for fusion. Step 420 may utilize methods and tools known in the art.

In an embodiment, step 420 implements a step 422 of performing the preparation of the intervertebral disc space lateral to the dura, inferior to the exiting nerve root, and superior to the inferior pedicle within the neural foramen. By performing all preparatory work in the neural foramen, any significant retraction of either the exiting or traversing nerve roots may be avoided and the intradiscal fusion may effectively be completed using a "no touch" technique. In one example of step 422, the disc annulus is incised within the neural foramen, well lateral to the dura. A variety of disc reamers, curettes, and rongeurs are passed within the disc space to evacuate the substance of the disc and denude the vertebral endplates of cartilage.

Optionally, step 420 includes a step 424 of applying a distraction tool through the retractor to distract the intervertebral disc space while using instrumentation (pedicle screws and optionally transfixing rod) on the non-working side to apply distraction to the spinal segment. This distraction may allow for further indirect decompression of neural elements on the working and the non-working side and may significantly assist in reduction of non-physiologic anatomy (as in spondylolisthesis and scoliosis).

In a step 430, the surgeon deposits fusion-promoting material in the intervertebral disc space. Step 430 may utilize methods and/or intervertebral cages known in the art.

Attached Exhibit A shows a non-limiting example of method 100 implementing methods 200, 300, and 400 to perform minimally invasive TLIF of a spinal segment. The example in Exhibit A utilizes the Mazor Renaissance® guidance system and the Hover T frame.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A minimally invasive transforaminal lumbar interbody fusion surgery method, comprising:
    placing a guide wire in each pedicle of each vertebra of each spinal segment to be fused in a transforaminal lumbar interbody fusion surgery;
    after the step of placing, preparing working side and non-working side of spine, said preparing including:
        for each guide wire on the working side of the spine except for a most superior guide wire, inserting a pedicle marker into the pedicle over the guide wire and removing the guide wire, and
        for each guide wire on the non-working side, screwing a pedicle screw into the pedicle over the guide wire and removing the guide wire; and
    after the step of preparing, surgically manipulating, from the working side, each spinal segment to be fused using the pedicle markers while each pedicle screw on the non-working side is in its respective pedicle.

2. The method of claim 1, further comprising:
    interconnecting each pedicle screw on the non-working side with a transfixing rod; and
    for each spinal segment to be fused:
        from the working side in the step of surgically manipulating, distracting the intervertebral disc space using a distracting tool inserted to the intervertebral disc space, and
        on the non-working side, manipulating the transfixing rod and at least one of the pedicle screws to apply distraction of the spinal segment.

3. The method of claim 2, comprising performing the steps of distracting and manipulating simultaneously to (i) apply distraction from the non-working side, using the transfixing rod and at least one of the pedicle screws, in synchrony with (ii) distraction from the working side using the distraction tool inserted to the intervertebral disc space.

4. The method of claim 2, the step of surgically manipulating further comprising, for each spinal segment to be fused:

positioning a retractor to form an access path from the working side to at least the intervertebral disc space; and in the step of distracting the intervertebral disc space, inserting the distraction tool through the retractor to the intervertebral disc space.

5. The method of claim 1, comprising performing the step of surgically manipulating while the most superior guide wire is in its respective pedicle.

6. The method of claim 1, further comprising, on the working side and for each spinal segment to be fused:

positioning a retractor to form an access path for the surgeon to portion of the spinal segment requiring surgery.

7. The method of claim 6, comprising, for each spinal segment to be fused, performing the step of surgically manipulating the spinal segment through the retractor.

8. The method of claim 7, the step of surgically manipulating comprising:

decompressing neural structures associated with the spinal segment;

preparing intervertebral disc space of the spinal segment for fusion; and depositing fusion-promoting material in the intervertebral disc space.

9. The method of claim 8, the step of decompressing comprising utilizing location of the pedicle marker in the inferior vertebra of the spinal segment to remove superior portion of working-side facet of the inferior vertebra.

10. The method of claim 8, further comprising:

interconnecting each pedicle screw on the non-working side with a transfixing rod;

in the step of preparing the intervertebral disc space, applying distracting tools through the retractor to distract the intervertebral disc space; and while preparing the intervertebral disc space, manipulating the transfixing rod and at least one of the pedicle screws on the non-working side to apply distraction of the spinal segment.

11. The method of claim 8, the step of preparing intervertebral disc space being performed lateral to dura, inferior to exiting nerve root of the spinal segment, and superior to the inferior pedicle of the spinal segment within neural foramen of the spinal segment.

12. The method of claim 7, further comprising after the step of surgically manipulating:

replacing each pedicle marker with a pedicle screw;

replacing the most superior guide wire with a pedicle screw; and interconnecting each pedicle screw on the working side with a transfixing rod.

13. The method of claim 12, further comprising, for each spinal segment to be fused, adjusting (a) spacing between the pedicle screws on the working side and (b) spacing between the pedicle screws on the non-working side.

14. The method of claim 1, the step of placing a guide wire in each pedicle comprising utilizing a robotic guidance system to place each guide wire according to a template generated from imaging of patient.

15. The method of claim 14, the step of utilizing a robotic guidance system further comprising utilizing robotic guidance to make at least one incision needed to perform the transforaminal lumbar interbody fusion surgery.

16. The method of claim 14, the step of utilizing a robotic guidance system comprising affixing the robotic guidance system to the patient with patient being in substantially same position as during said imaging.

17. The method of claim 16, the step of affixing comprising affixing the robotic guidance system to (a) spinous process superior to each spinal segment to be fused and (b) both iliac crests of the patient.

18. The method of claim 16, further comprising removing the guidance system from the patient prior to the step of performing.

19. The method of claim 18, further comprising after the step of placing a guide wire in each pedicle and before the step of removing the guidance system, imaging patient to confirm proper location of each guide wire.

20. The method of claim 1, for each spinal segment to be fused, the step of surgically manipulating including at least one of removing soft tissue from the spinal segment, distracting intervertebral disc space, and placing fusion promoting material in the intervertebral disc space.

* * * * *